United States Patent [19]

Dick et al.

[11] Patent Number: 5,520,811

[45] Date of Patent: May 28, 1996

[54] METAL ACCUMULATION

[75] Inventors: Rosemary E. Dick, Harborne; Lynne E. Macaskie, Headington, both of England

[73] Assignee: British Nuclear Fuels PLC, Warrington, England

[21] Appl. No.: 436,205

[22] PCT Filed: Nov. 12, 1993

[86] PCT No.: PCT/GB93/02330

§ 371 Date: Jun. 28, 1995

§ 102(e) Date: Jun. 28, 1995

[87] PCT Pub. No.: WO94/11315

PCT Pub. Date: May 26, 1994

[30] Foreign Application Priority Data

Nov. 14, 1992 [GB] United Kingdom ............... 9223932

[51] Int. Cl.$^6$ .............................. C02F 3/34; C02F 1/62; C02F 1/64; C12N 9/12

[52] U.S. Cl. .................. 210/606; 210/611; 210/630; 210/631; 210/632; 210/906; 210/912

[58] Field of Search .................. 210/605, 606, 210/610, 611, 629-631, 906, 912-914; 435/823, 827, 262.5

[56] References Cited

U.S. PATENT DOCUMENTS

| | | | |
|---|---|---|---|
| 3,980,557 | 9/1976 | Yall et al. | 210/611 |
| 4,029,575 | 6/1977 | Bykowski et al. | 210/605 |
| 4,043,910 | 8/1977 | Field et al. | 210/906 |
| 4,780,208 | 10/1988 | Bohnke et al. | 210/605 |
| 5,252,214 | 10/1993 | Lorenz et al. | 210/605 |
| 5,397,473 | 3/1995 | Jewell | 210/610 |

FOREIGN PATENT DOCUMENTS 3729127  3/1989  Germany.

OTHER PUBLICATIONS

Wasser, Abwasser, No. 6, 1991, Verlag R. Oldenbourg Munchen, M. Streichan et al "Polyphosphatspeichernde Bakterien" pp. 301–307.

Water Research, vol. 20, No. 12, Dec. 1986 Pergamon Journals Ltd., Y. Comeau et al. "Biochemical model for enhanced biological".

Journal of Chemical Technology & Biotechnology, vol. 49, No. 4, 1990 L. Macaskie "An Immobilized Cell Bioprocess for the Removal of heavy Metals from Aqueous Flows", pp. 357–379, p. 360 lines 18–36; p. 367, fig. 5; p. 369 last paragraph; p. 70, table 7.

*Primary Examiner*—Thomas G. Wyse
*Attorney, Agent, or Firm*—Jacobson, Price, Holman & Stern

[57] ABSTRACT

Metals have phosphates of low water solubility e.g. Cd, Pb, Cu, Mn, Sr, U, La, Pu, Am and Np, are removed from water by reaction with phosphate produced by enzymatically-cleaved polyphosphate which has been accumulated by one or more polyphosphate-accumulating microorganisms.

10 Claims, 15 Drawing Sheets

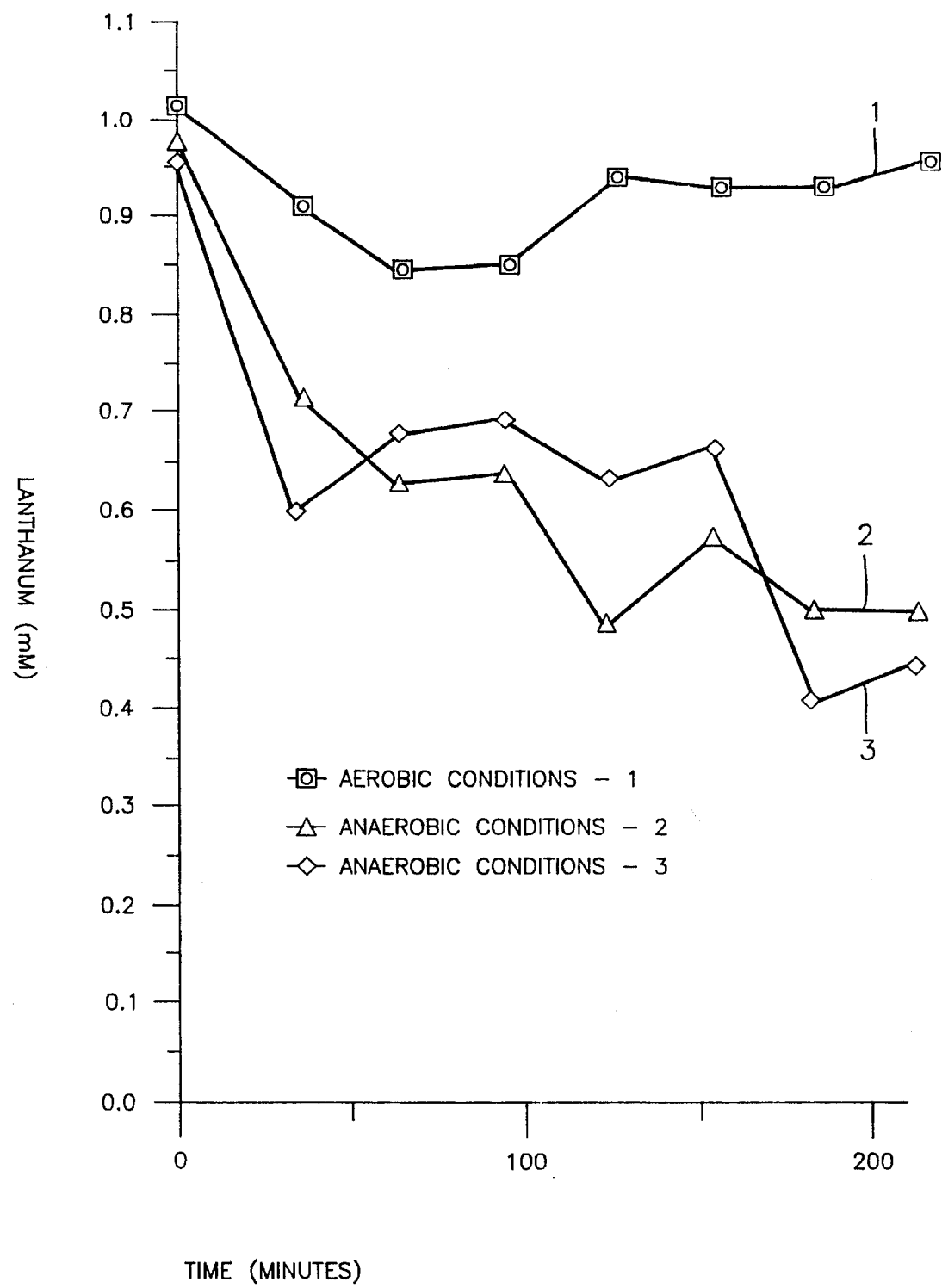

ANAEROBIC PERIOD

METAL ACCUMULATION

This invention relates to metal accumulation and is more particularly concerned with the removal of metals from water containing such metals, for example, for one or more of the following purposes:

(a) water purification, (b) recovering of metals from water which is used in a washing or other process, for example water which has been used in the treatment of precious metal ores, and (c) accumulation of heavy metals from water which has been used to treat soils for the purpose of removing heavy metals from such soils.

It has been previously proposed in "An immobilised cell bioprocess for the removal of heavy metals from aqueous flows", L. E. Macaskie, J. Chem. Technol. Biotechnol. 49 357–379 (1990), to effect heavy metal removal using Citrobacter sp. wherein the biomass is cultivated using glycerol-2-phosphate to prepare the biomass cells in the correct physiological state for metal removal. Metal removal relies upon the co-presentation of the metal with glycerol-2-phosphate (G2P) in an amount of up to 5 mM as a phosphate donor for metal accumulation by the immobilised cells. The G2P is enzymically cleaved to glycerol (a potential energy source for the cells) and inorganic phosphate, an efflux of which intercepts the incoming metal and results in the precipitation of crystalline heavy metal phosphate. Whilst such process is efficient in removal of heavy metals from solution, it has the disadvantage that it uses expensive glycerol-2-phosphate.

It is an object of the present invention to provide a technique which does not rely on the use of an expensive medium such as glycerol-2-phosphate.

In one of its aspects, the present invention resides in the use of one or more polyphosphate-accumulating microorganisms to accumulate polyphosphate which is then enzymatically cleaved in the presence of water containing one or more metals to produce phosphate ions which react with the metal(s) in the water in order to precipitate metal phosphate. Such metal phosphate may be crystalline or it may be mixed with other precipitated species such as the hydroxide.

In another of its aspects, the present invention resides in the use of phosphate ions produced upon cleavage of polyphosphate to remove metal(s) from solution by precipitation as metal phosphate(s).

Metals which are susceptible to the techniques of the present invention are those having a phosphate of low water solubility, for example, cadmium, lead, copper, manganese, cobalt, nickel, calcium, yttrium, strontium, uranium, lanthanum, lanthanides, plutonium, americium and neptunium.

In a preferred process, a polyphosphate-accumulating microorganism is cultivated in a culture medium under conditions where the microorganism can synthesise and utilise adenosine triphosphate (ATP), and then ATP synthesis/utilisation is modified whereby to cause the microorganism to utilize polyphosphate as an alternative energy source resulting in the production of said phosphate ions which can then react with the metal ions to produce precipitation of metal phosphate.

The microorganism is preferably a polyphosphate-accumulating bacterium, and may, for example, be polyphosphate-accumulating Acinetobacter bacterium. It is known per se (see Y. Comeau et al, Wat. Res. vol.20, No. 12, pp 1511–1521) (a) that certain microorganisms are capable of accumulating polyphosphate reserves under aerobic conditions and of utilising such polyphosphate under anaerobic conditions to produce phosphate; and (b) that this can be used to induce biological phosphorus removal in an activated sludge treatment by providing an anaerobic treatment zone upstream of the standard aerobic process. However, as far as we are aware, it has never been previously proposed to utilise the polyphosphate accumulated by such microorganisms as a source of phosphate for removing heavy metals from solution. Thus, the present invention relies on the use of polyphosphate as the main source of phosphate for metal accumulation via enzymically mediated metal bioaccumulation or biomineralisation.

A particular example of a known polyphosphate-accumulating Acinetobacter bacterium is *Acinetobacter calcoaceticus* ATCC 23055 (NCIMB 10694). Another example of a known polyphosphate-accumulating microorganism is *Klebsiella pneumoniae* ATCC 12658 (=NCIMB 8806).

In the case of Acinetobacter, synthesis/utilisation of ATP is possible under aerobic conditions, and switching off energy utilisation from ATP is possible by a switch to anaerobic conditions. Under anaerobic conditions, ATP utilisation is inhibited by inhibiting ATP synthesis as it is normally understood to occur under normal (aerobic) conditions. However, it is within the scope of the present invention to switch off ATP utilization by addition of an uncoupling agent which interferes with ATP synthesis, for example 2,4-dinitrophenol or DCCD (dicyclohexyl carbodiimide).

Preferred bacteria are Acinetobacter sp. W6 and Acinetobacter sp. W9 which we have isolated from activated sludge as described hereinafter and have deposited under the provisions of the Budapest Treaty with The National Collection of Industrial and Marine Bacteria Limited (NCIMB) of 23 St. Machar Drive, Aberdeen AB2 1RY, Scotland, under the respective Accession Numbers NCIMB 40594 and NCIMB 40595 on 5 Nov. 1993.

The presently available indications (as observed from growth on Lab M nutrient agar and incubated at 25° C.) of these deposited bacteria are as follows:

| Species code | W6 | W9 |
| --- | --- | --- |
| Cell morphology (× 630) | coccobacilli in pairs | large cocci, pairs |
| Gram stain | (−) | variable |
| Spores | (−) | (−) |
| Motility | (−) | (−) |
| Colony morphology | circular, crenated, flat, buff, opaque, smooth, 2 mm dia. 7 days | circular, eroded, buff, low convex, semi-translucent, central concentric ring 1½–2 mm dia. 7 days |
| °C. growth | 37° C. (−) | 37° C. (+) |

| Species code | W6 | W9 |
| --- | --- | --- |
| | 41° C. (−) | 41° C. (−) |
| | 45° C. (−) | 45° C. (−) |
| Polyphosphate | (+) | (+) |
| Catalase | (+) | (+) |
| Oxidase | (−) | (−) |
| Acid produced in Glucose OF medium | (−) | (−) |

We have also found that the present invention does not require the polyphosphate-accumulating microorganism to be isolated from the environment in which it occurs. In particular, we have found that activated sludge containing polyphosphate-accumulating microorganisms can be employed per se in the present invention. A suitable type of activated sludge is one which is used in a plant for removing phosphorus ions from effluent liquor (eg by the so-called "Phostrip" or "Phoredox" process) before discharge into the environment.

It will be appreciated that the techniques of the present invention rely on a supply of phosphorus. Such supply may be provided by at least partly by deliberate addition of an assimilable source of phosphorus. However, it will be appreciated that the present invention is applicable to the removal of metal(s) from water which already contains an assimilable source of phosphorus as an impurity but which is not in a form in which it can react directly with the metal(s) impurity also present in the water or in which the metal impurity is not in a form in which it can react with the phosphorus.

The operating conditions in the aerobic and anaerobic phases of the process are the normal conditions which are used for aerobic and anaerobic treatments involving the use of microorganisms. However, it is preferred to use low nitrate concentrations in the anaerobic phase since reduction of nitrate to nitrite can substitute for oxygen and may then inhibit the required conversion of polyphosphate to phosphate. Typically the temperature will be in the range of 0° to 36° C., most preferably from 15° to 30° C. The medium used in the aerobic cultivation of the microorganism is a suitable growth medium containing assimilable carbon, nitrogen, phosphorus and other necessary trace elements for optimum growth. Such medium may be a waste from another process. There is no need to use expensive sources of carbon and phosphorus, such as G2P.

Under the anaerobic conditions, there may be no need to provide such nutrients, merely a need to provide suitable anaerobic conditions by ensuring that dissolved oxygen and oxidised nitrogen (nitrite and nitrate) are absent.

A typical method for removal of heavy metals from waste water in accordance with the present invention will now be described.

Representative strains of polyphosphate-accumulating Acinetobacter sp. are grown aerobically and immobilised on a solid support (eg open-pore polyurethane foam, glass beads, sand or gravel-type materials) in a bioreactor using an aqueous nutrient medium which is circulated through the bioreactor. Gaseous oxygen is introduced via a compressed air feed and bubble breaking device. The nutrient medium contains waste fermentation products and waste phosphate from phosphate-rich waste water as assimilable carbon, nitrogen and phosphorus sources. The aerobic treatment is effected at a temperature of about 20° C. and a pH of 7.0 for 24–48 hours so as to accumulate polyphosphate.

Following this, the conditions in the bioreactor are switched to anaerobic conditions where no nutrients or assimilable oxygen are supplied. The waste water containing the heavy metals to be removed is passed through the bioreactor so as to contact the immobilised bacteria containing the accumulated polyphosphate. Under the anaerobic conditions, the bacteria are deficient in their supply of ATP and thus start to utilise the accumulated polyphosphate as an energy source. The result of this is that the polyphosphate is enzymically cleaved to produce phosphate which reacts with the heavy metals to precipitate heavy metal phosphate, thus removing heavy metals or at least reducing the heavy-metal concentration in the water.

Following this, the bioreactor can then be switched back to operate aerobically so that the process can be performed cyclically with periodic shut-down to replace the microorganism when it has become non-viable. During each anaerobic phase, the micro-organism may also produce the carbon storage polymer, polyhydroxybutyrate (PHB) with a suitable carbon supply, which can be utilised as a source of stored carbon for growth and to generate ATP to fuel further accumulation of polyphosphate during the succeeding aerobic cycle.

The present invention will now be described in more detail in the following experiments.

In the accompanying drawings:

FIG. 1a is a graph in which phosphate ion and lanthanum ion concentrations in solution are plotted against time during inorganic precipitation of lanthanum phosphate in a cell-free solution, FIG. 1b is a graph in which phosphate ion and uranyl ion concentrations in solution are plotted against time during incubation in a cell-free solution, FIGS. 2a and 2b are charts tabulating the results given respectively in Tables 1 and 2 below, FIG. 3a is a graph showing phosphate released by Acinetobacter calcoaceticus NCIMB 10694 where phosphate concentration is plotted against time, FIG. 3b is a graph showing lanthanum removal by Acinetobacter calcoaceticus NCIMB 10694 where lanthanum concentration is plotted against time, FIG. 4 is a graph showing phosphate release by strain W9 under anaerobic conditions in the presence and absence of $La^{3+}$, and removal of lanthanum, where phosphate and lanthanum concentrations are plotted against time, FIG. 5 is a graph showing removal of lanthanum and phosphate release by cell suspensions of strain W6 incubated under anaerobic conditions, where phosphate and lanthanum concentrations are plotted against time, FIGS. 6 to 9 are charts tabulating the results given respectively in Tables 3 to 5 below, FIGS. 10 and 11 show the phosphate and metal levels in the first and second reactors respectively throughout one aerobic and one anaerobic period for two consecutive days in Experiment 8 below, and FIG. 12 is an X-ray diffraction spectrum of a sample obtained from the second reactor used in Experiment 8 as compared with that for pure $H_2(UO_2)_2(PO_4)_2 8H_2O$.

In the experiments below, the following growth media were employed:

| Medium 1 - growth medium per litre | |
|---|---|
| Tris | 6.0 g |
| sodium acetate | 5.0 g |
| $(NH_4)_2SO_4$ | 1.5 g |
| $MgSO_4.7H_2O$ | 0.16 g |
| $CaCl_2.2H_2O$ | 0.08 g |
| KCl | 0.6 g |
| trace elements solution[a] | 1.0 ml |
| ferrous EDTA solution[b] | 0.25 ml |

The pH was adjusted to 7.1 with HCl and the medium was sterilised by autoclaving. The following were sterilised separately and added after cooling:

| 10% yeast extract | 1 ml |
|---|---|
| $K_2HPO_4.3H_2O$ | 0.16 g |
| [a]Trace elements solution contained (per litre): | |
| $ZnSO_4.7H_2O$ | 10 mg |
| $MnCl_2.4H_2O$ | 3 mg |
| $H_3BO_3$ | 30 mg |
| $CoCl_2.6H_2O$ | 20 mg |
| $CuCl_2.2H_2O$ | 1 µg |
| $NiCl_2.6H_2O$ | 2 mg |
| $Na_2MoO_4.2H_2O$ | 3 mg |

[b]Ferrous EDTA solution contained ferrous sulphate (heptahydrate) ethylenediaminetetra-acetic acid disodium salt, (commercially obtained mixture) 1.0 g/l]

Medium 2-nitrogen-limiting growth medium

As Medium 1 but containing (per litre) 10 g sodium acetate and 0.23 g

| Medium 3 - Aerobic phase medium per litre | |
|---|---|
| Tris | 6.0 g |
| sodium acetate | 0.36 g |
| $(NH_4)_2SO_4$ | 0.02 g |
| $MgCl_2.6H_2O$ | 0.03 g |
| $CaCl_2.2H_2O$ | 0.02 g |
| KCl | 0.012 g |
| $K_2HPO_4.3H_2O$ | 0.136 g (autoclaved separately) |

$K_2HPO_4.3H_2O$.

The pH was adjusted to 7.1 with HCl and the medium was sterilised by autoclaving.

| Medium 4 - Anaerobic phase medium (final concentrations) | |
|---|---|
| MOPS (3-(N-morpholino)propane sulphonic acid)/ NaOH buffer pH 7.0 | 40 mM |
| Citric acid/trisodium citrate buffer pH 7.0 | 2 mM |
| sodium acetate (sterilised by autoclaving) | 10 mM |

MOPS was replaced in some experiments with Tris/HCl buffer at the same pH and concentration. In experiments with uranyl ions, sodium acetate was replaced with 10 mM ammonium acetate.

Unless otherwise stated all experiments were incubated at 30° C.

Isolation of microbial strains W6 and W9

Activated sludge mixed liquor was obtained from Severn Trent sewage treatment works (located at Wimborne, England). An homogenous suspension of each liquor was made and serial dilutions (in sterile saline, 0.85% w/v) were plated onto nutrient agar (Difco Laboratories, Detroit, USA). After 2 weeks incubation at room temperature (20° C.), colonies with distinctly different morphologies were chosen, removed from the $10^{-4}$ to $10^{-6}$ dilutions and were streaked to purity on nutrient agar. Following Gram stains and oxidase tests, the isolated microorganism strains (W6 and W9) were tentatively identified using API 20E and 20NE identification strips (API System, bioMérieux SA, France) as being of the genus Acinetobacter. The strains W6 and W9 have been deposited under the provisions of the Budapest Treaty with The National Collection of Industrial and Marine Bacteria Limited (NCIMB) under the respective Accession Numbers NCIMB 40594 and NCIMB 40595 on 5 Nov. 1993.

Methods (a) Experiments with free cells

A 50 ml starter culture of medium 1 was inoculated and incubated for 1–2 days. 20 ml of this was used to inoculate 2 litres of medium 2 and the culture was incubated aerobically with forced aeration from a compressed air supply for 24–36 hours. Cells were harvested by centrifugation (4500 rpm; 4° C.; 30 mins). The supernatant was poured off and a portion of it used to resuspend the cells. Each suspension was centrifuged again. The cell pellets were again resuspended in a portion of the supernatant, the cell suspensions were combined and chilled on ice before use. The combined cell suspension was used to inoculate medium 4, with or without the addition of metal salts as described in individual experiments. Air or nitrogen gas (oxygen-free) was bubbled through the medium depending upon whether aerobic or anaerobic conditions were required. At intervals, 1 ml of the incubation mixture was removed and the cells rapidly sedimented by centrifugation (12000 rpm; 5 mins). The supernatant was assayed for phosphate and metal.

(b) Experiments with immobilised cells

Cultures of up to 4 litres were grown and harvested as described for experiments with free cells. The cell pellets were weighed, resuspended in 0.85% NaCl and combined into aliquots. The cells were immobilised variously in agar or agarose (3% w/v final concentration; final cell concentration approximately 5% w/v) with, in some experiments, the formation of beads (mean diameter 1 mm) according to the method of Nilsson et al (Eur. J. Appl. Microbiol. Biotechnol. 17:319–326), soy oil being used for the hydrophobic phase. In other experiments, the gelled cell suspension was set in a mould and the solidified gel was shredded by passing through a stainless mesh to give extruded particles of 1 mm square cross-section and up to 10 mm in length. The gel particles or beads were washed in saline to remove non-immobilised cells and/or adherent oil and were placed in a pre-sterilised reactor vessel or column. Here they were incubated in alternating anaerobic and aerobic phases (medium 4 and 3 respectively) with or without metal in the anaerobic phase as described below.

Chemical Analyses

Cadmium and lead were detected by ASV (anodic stripping voltametry) with a hanging drop mercury electrode using a Metrohm 693 VA polarographic and voltametric analyser. Lanthanum and uranyl were detected by colorimetric determination with arsenazo III in acidic solution (M. R. Tolley, D.Phil. Thesis Univ of Oxford, 1993). Phosphate was determined colorimetrically by its reaction with acidified molybdate (Pierpont 1957 Biochem J. 65:67–76). X-ray powder diffraction data were obtained on a Picker Precision diffractometer with an incident beam monochromator (Germanium III planes), Phillips PN1710 diffractometer control unit and Siemens/Socabin DIFFRAC/AT program suite. Exposure times were 16 hours to CuKα radiation ($\lambda=1.5406\text{Å}$).

Details of Reactors

1) Automated Reactors

Two reactors of 500 ml maximum volume containing 150 g of 4 mm diameter glass beads to act as a filter for particulates were employed. Pumps and electrically operated valves allowed automated operation of a fill-and-draw system of alternating aerobic and anaerobic periods, and were controlled by timers subjecting the reactors to three 8-hour cycles daily. Influent medium and reactors were autoclaved before use, whilst tubing and valves were sterilised with 70% ethanol and washed with sterile distilled water.

Each 8-hour cycle was as follows:

| Time (minutes) | |
|---|---|
| 0–150 | Incubation in anaerobic phase (medium 4; nitrogen gas bubbled through medium at slow rate to keep headspace anoxic) |
| 150–161 | Draw phase - medium 4 drawn off; nitrogen on |
| 161–166 | Fill phase - medium 3 (aerobic medium) filled; nitrogen off/air bubbled through medium at high rate |
| 166–464 | Incubation in aerobic phase; air on |
| 464–476 | Draw phase - medium 3 drawn off; air on |
| 476–480 | Fill phase - Medium 4 filled; air off/nitrogen on |

The three anaerobic periods daily were at the following times: 06.30–09.00; 14.30–17.00 and 22.30–01.00. Samples were taken for analysis at the end of the first and second anaerobic periods daily and, when appropriate, throughout the first aerobic and second anaerobic phases (09.00–17.00). The third anaerobic phase was not sampled.

The approximate volume delivered to each reactor was 200 ml of medium 4 for the anaerobic phase and 250 ml of medium 3 for the aerobic phase (influent flow rate=50 ml/minute; effluent flow rate=20.8 ml/minute)

For phosphate and metal analysis throughout the aerobic and anaerobic phases, 2–4 ml samples were drawn off with a syringe by means of a sampling tube. The medium was allowed to settle before metal analysis but for phosphate analysis was centrifuged to remove suspended cells, and the supernatant analysed. Phosphate release during the anaerobic phase was determined as the difference between samples at the beginning and end of the anaerobic phase. For calculation of metal removal, samples of the effluent were allowed to settle for 5 minutes and the metal concentration compared with that of the influent medium.

2) Column Reactors

A variable-speed pump with a manual reverse function and manually operated valves allowed changing of medium between the aerobic and anaerobic phases aseptically. Column reactors were subjected to two anaerobic phases each of 2.5 hours daily (at roughly the same times each day—9.30–12.00 and 16.00–18.30). Glass beads (2 mm diameter) were used as a filter in the base of each column. The total volume in each phase was 250 ml. During the change between phases, one medium was drawn off and the other medium filled in less than 5 minutes per column. For metal analysis, the settled effluent was compared with the influent medium. To sample residual phosphate in the column at the start of the anaerobic phase, a sample of the medium was taken by first drawing off 10–15 ml medium through a sampling tube to ensure that stagnant liquid in the sampling tube was washed out, then a further 5 ml sample was taken and subjected to centrifugation and analysis of the supernatant; this was compared with the phosphate in the effluent supernatant.

EXPERIMENT 1

Comparison—inorganic precipitation of metal phosphates in a cell-free solution

Lanthanum nitrate (1 mM) and uranyl nitrate (1 mM) were incubated in the presence of 0.5 mM of inorganic phosphate (as $K_2HPO_4$) in medium 4 with nitrogen sparging to ensure anaerobic conditions. At intervals, samples were removed, centrifuged (12000 rpm, 5 mins) and the supernatants analysed for remaining phosphate and metal ion.

EXPERIMENT 2

Figure 1A:
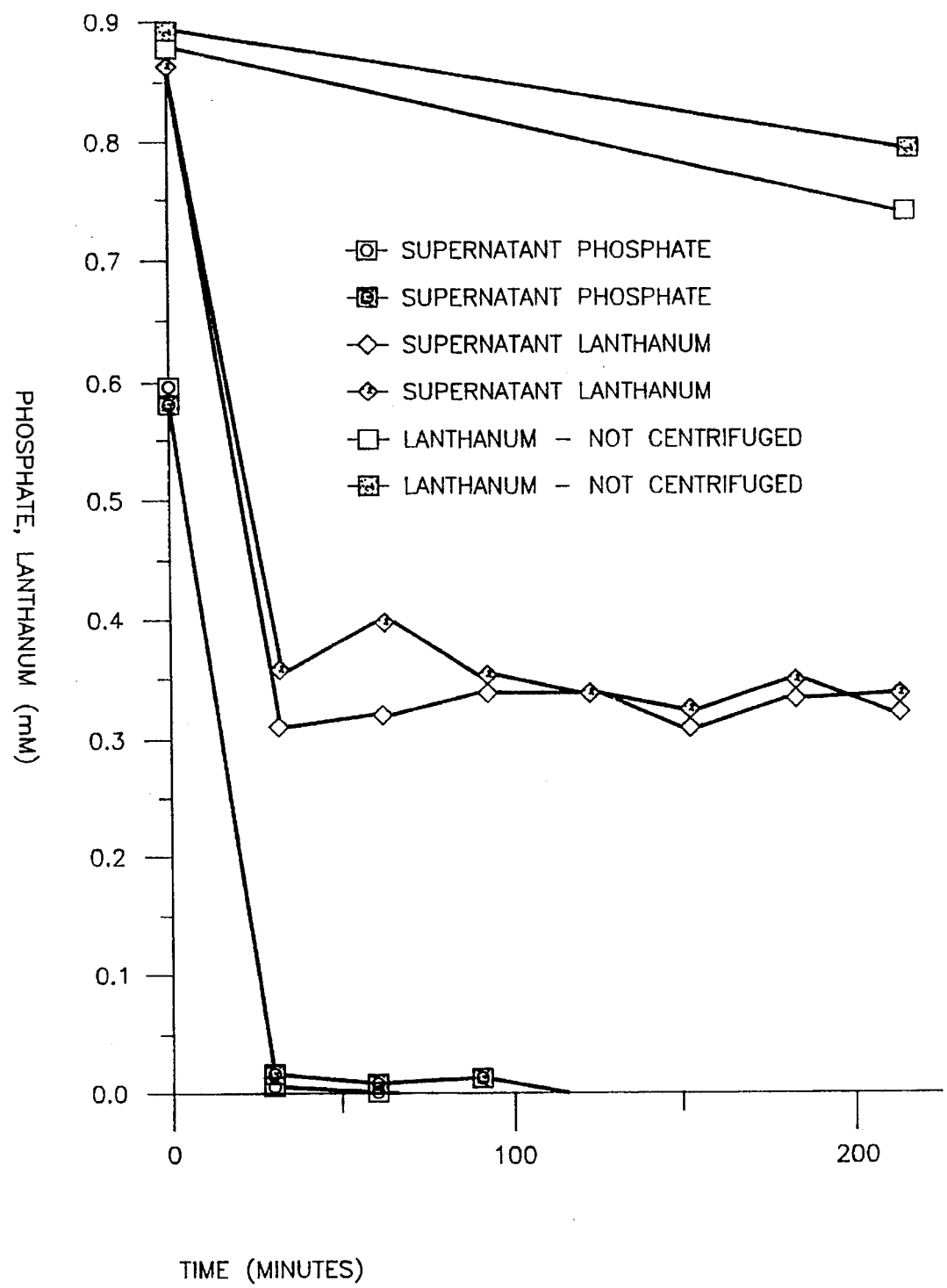
FIG. 1a shows the rapid loss of lanthanum from solution due to the precipitation of lanthanum phosphate. However the precipitate is fine and remains in suspension without centrifugation.
Figure 1B:
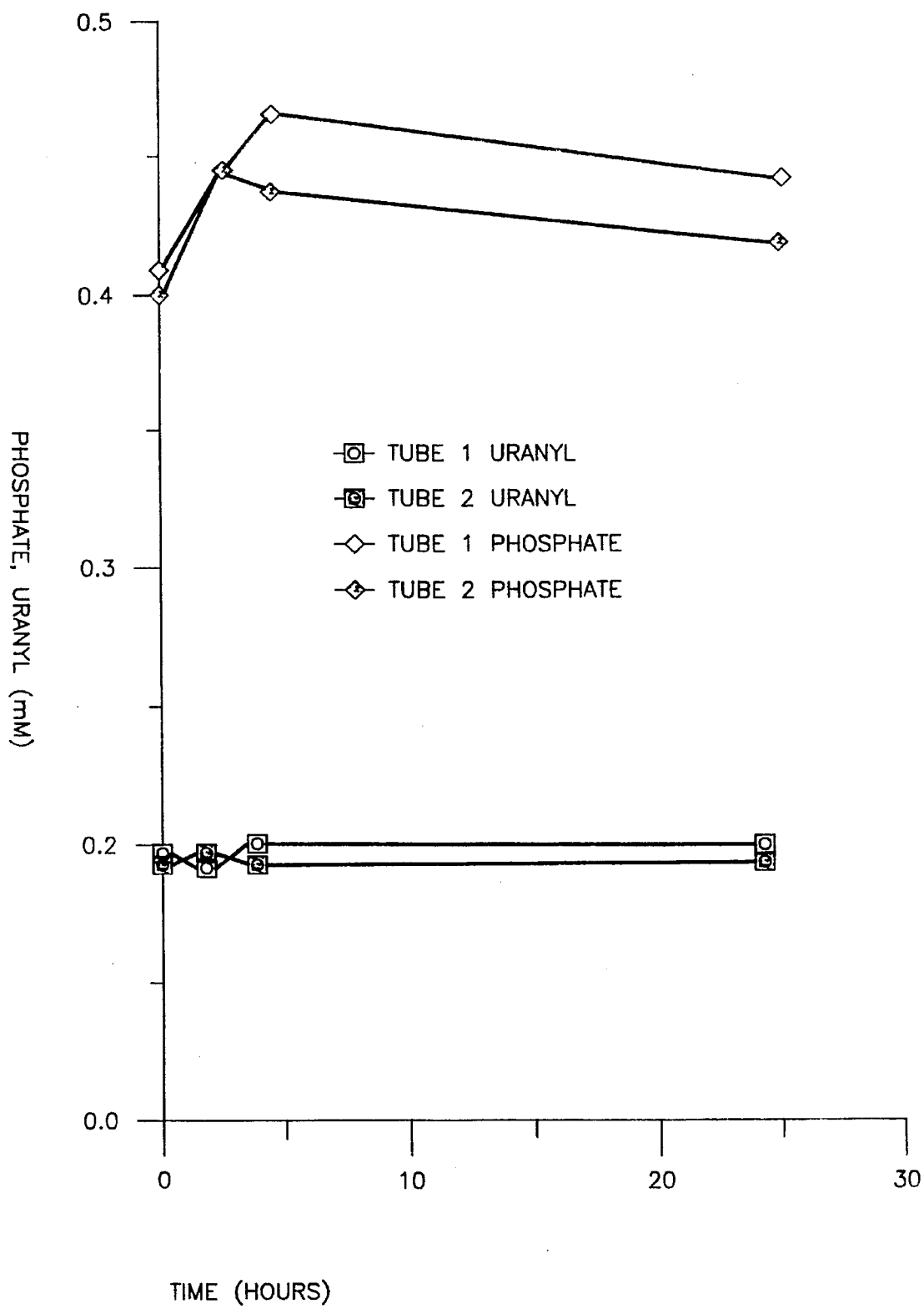
FIG. 1b shows that the uranyl ion $UO_2^{2+}$) does not readily produce a precipitate which can be removed from suspension by centrifugation.

Phosphate release and metal removal by a phosphate-removing activated sludge

Raw activated sludge or so-called "mixed liquor" was obtained from a nutrient plant operating a "Phostrip" Process. The total suspended solids of the mixed liquor was 6.43 g/l. 350 ml of the mixed liquor was used to inoculate each of the two automated reactors. This was topped up with 50 ml of medium 4 (without added metal), and the initial anaerobic phase incubation begun. The reactors were initially operated without metal in the influent medium 4, then cadmium or lead acetate (0.2 mM), or lanthanum nitrate (0.5 mM), was added as shown in Tables 1 and 2 below

TABLE 1

Phosphate release and lead and lanthanum removal in the first reactor
3 anaerobic periods per day, samples only from 2(9:00 am and 5:00 pm)

| Day | Time | Polarography | | | | | | Colourimetric determination | | |
|---|---|---|---|---|---|---|---|---|---|---|
| | | mM $PO_4$ released | influent mg $Pb^{2+}$/l | influent mM $Pb^{2+}$ | effluent mg $Pb^{2+}$/l | effluent mM $Pb^{2+}$ | mM $Pb^{2+}$ removed | influent mM $La^{3+}$ | effluent nM $La^{3+}$ | mM $La^{3+}$ removed |
| 1 | am | | 0 | | | | | 0 | | |
| | pm | 0.293 | 0 | | | | | 0 | | |
| 2 | am | 0.123 | 0 | | | | | 0 | | |
| | pm | 0.216 | 0 | | | | | 0 | | |
| 3 | am | nt | 65.7 | 0.32 | 3.78 | 0.02 | 0.30 | 0 | | |
| | pm | nt | 65.7 | 0.32 | 2.42 | 0.01 | 0.31 | 0 | | |
| 4 | am | nt | 65.7 | 0.32 | 4.47 | 0.02 | 0.30 | 0 | | |
| | pm | 0.122 | 0 | 0.00 | 0 | 0.00 | 0.00 | 0 | | |
| 5 | am | nt | 65.7 | 0.32 | 9.52 | 0.05 | 0.27 | 0 | | |
| | pm | 0.119 | 0 | | | | | 0 | | |
| 6 | am | 0.189 | 0 | | | | | 0 | | |
| | pm | nt | 0 | | | | | 0.485 | 0.35 | 0.137 |
| 7 | am | nt | 0 | | | | | 0.485 | 0.22 | 0.263 |
| | pm | nt | 0 | | | | | 0.485 | 0.21 | 0.273 |
| 8 | am | nt | 0 | | | | | 0.584 | 0.39 | 0.197 |
| | pm | nt | 0 | | | | | 0.584 | 0.50 | 0.088 |
| 9 | am | nt | 0 | | | | | 0.584 | 0.27 | 0.311 |
| | pm | nt | 0 | | | | | 0.584 | 0.16 | 0.426 |
| 10 | am | nt | 0 | | | | | 0.584 | 0.12 | 0.464 |
| | pm | nt | 0 | | | | | 0.584 | 0.17 | 0.415 |
| 11 | am | nt | 0 | | | | | 0.545 | nt | |
| | pm | nt | 0 | | | | | 0.545 | 0.06 | 0.486 | nt = not tested
Day 1 = anaerobic periods 1–3
Day 2 = anaerobic periods 4–6

TABLE 2

Phosphate release and cadmium and lanthanum removal in the second reactor
3 anaerobic periods daily, samples at 9:00 am and 5:00 pm only

| Day | Time | Polarography | | | | | | Colourimetric determ. | | |
|---|---|---|---|---|---|---|---|---|---|---|
| | | mM $PO_4$ released | influent mg $Cd^{2+}$/l | influent mM $Cd^{2+}$ | effluent mg $Cd^{2+}$/l | effluent mM $Cd^{2+}$ | mM $Cd^{2+}$ removed | influent mM $La^{3+}$ | effluent nM $La^{3+}$ | mM $La^{3+}$ removed |
| 1 | am | | 0 | | | | | 0 | | |
| | pm | 0.408 | 0 | | | | | 0 | | |
| 2 | am | 0.279 | 0 | | | | | 0 | | |
| | pm | 0.071 | 0 | | | | | 0 | | |
| 3 | am | nt | 33.68 | 0.30 | 12.81 | 0.11 | 0.19 | 0 | | |
| | pm | nt | 33.68 | 0.30 | 13.89 | 0.12 | 0.18 | 0 | | |
| 4 | am | nt | 33.68 | 0.30 | 14.76 | 0.13 | 0.17 | 0 | | |
| | pm | 0.077 | 0 | 0.00 | 0 | 0.00 | 0.00 | 0 | | |
| 5 | am | nt | 33.68 | 0.30 | 13.78 | 0.12 | 0.18 | 0 | | |
| | pm | 0.154 | 0 | | | | | 0 | | |
| 6 | am | 0.199 | 0 | | | | | 0 | | |
| | pm | nt | 0 | | | | | 0.485 | 0.27 | 0.219 |
| 7 | am | nt | 0 | | | | | 0.485 | 0.16 | 0.327 |
| | pm | nt | 0 | | | | | 0.485 | 0.14 | 0.35 |
| 8 | am | nt | 0 | | | | | 0.584 | 0.41 | 0.176 |
| | pm | nt | 0 | | | | | 0.584 | 0.37 | 0.213 |
| 9 | am | nt | 0 | | | | | 0.584 | 0.14 | 0.447 |
| | pm | nt | 0 | | | | | 0.584 | 0.20 | 0.387 |
| 10 | am | nt | 0 | | | | | 0.584 | 0.30 | 0.284 |
| | pm | nt | 0 | | | | | 0.584 | 0.27 | 0.317 |
| 11 | am | nt | 0 | | | | | 0.545 | nt | |
| | pm | nt | 0 | | | | | 0.545 | 0.05 | 0.492 | nt = not tested

Figure 2A:
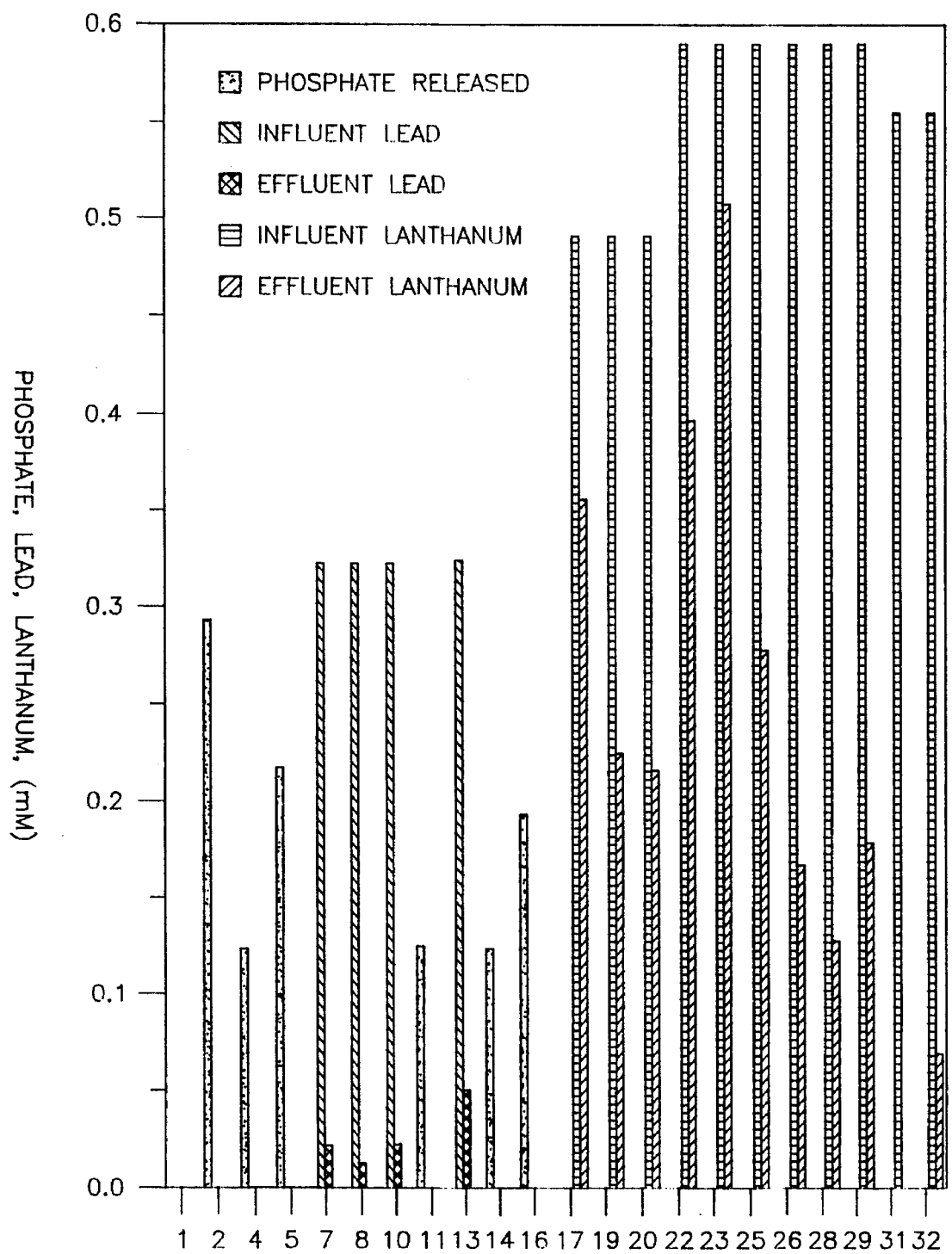
Figure 2B:
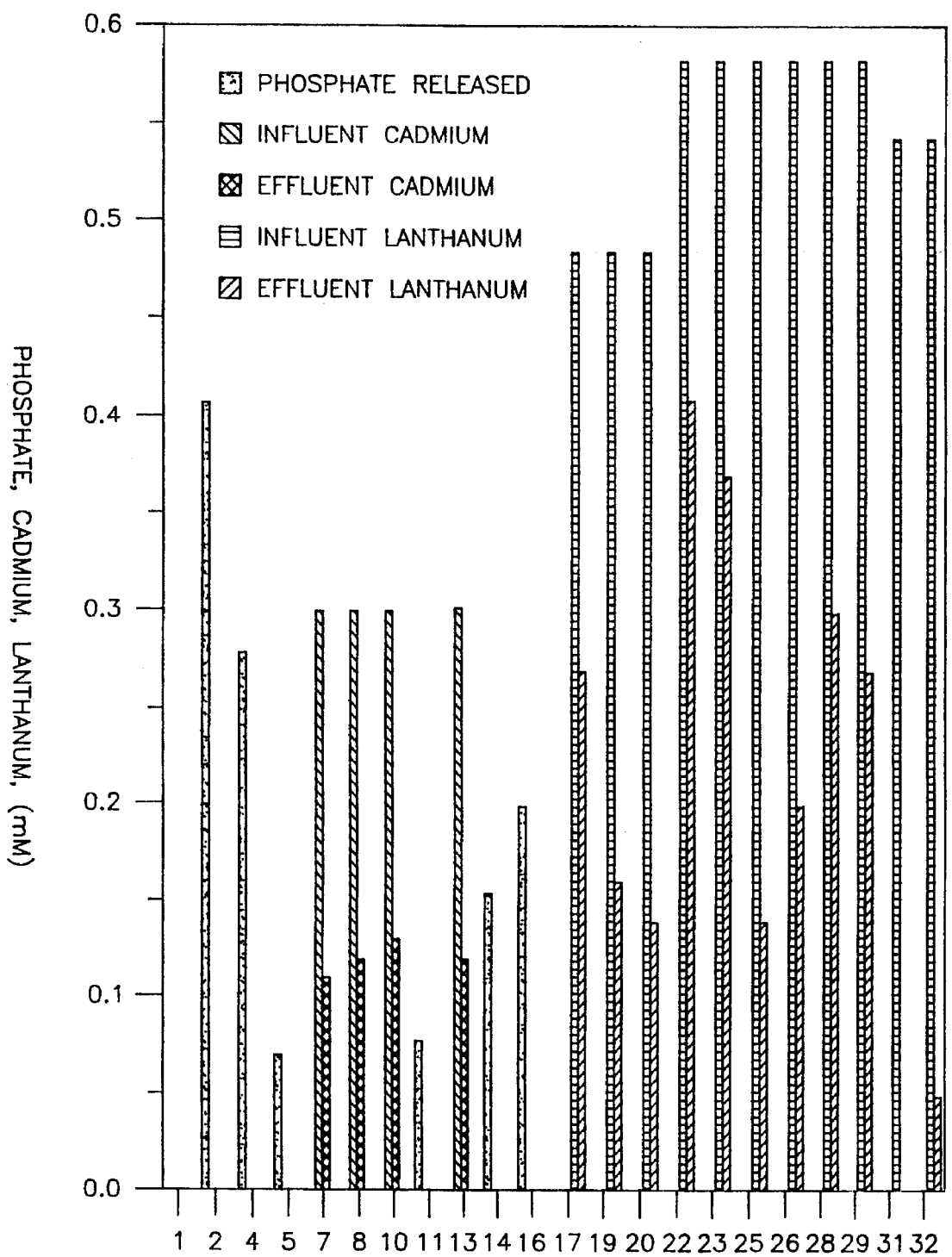

The results given in Tables 1 and 2 above are tabulated in enclosed FIGS. 2a and 2b, respectively.

EXPERIMENT 3

Comparison of the polyphosphate storage capacity in strains W6 and W9 isolated from activated sludge in comparison with the culture collection strain *Acinetobacter calcoaceti-* cus NCIMB 10694

Cells were grown and harvested as described previously. A cell suspension containing approx 1.0 g cells (wet weight) was loaded onto pre-formed Percoll density gradients and centrifuged at 9000 rpm for 30 minutes. The cells formed a band according to their density (specific gravity) which was determined against marker beads of known density (more polyphosphate=higher cell density); during subsequent incubation at 30° C., polyphosphate was degraded and the band of cells was seen to move up the gradient as the cells became less dense. The decrease in density is a measure of the short-chain polyphosphate which may be readily degraded under anaerobic conditions.

| Strain | initial density | density after 48–74h incubation |
|---|---|---|
| 10694 | 1.050–1.075 | 1.033–1.035 |
| W6 | 1.098–1.110 | 1.065–1.069 (2 populations) |
| W9 | 1.095 | 1.045 |

EXPERIMENT 4

Lanthanum removal by cell suspensions of *Acinetobacter calcoaceticus* NCIMB 10694

A culture of *Acinetobacter calcoaceticus* NCIMB 10694 was harvested after 24 h growth at an optical cell density ($OD_{600}$) of 0.370. The wet weight of the cell pellet obtained was 2.243 g and this was resuspended in a total volume of 6 ml. 1 ml of the suspension was added to tubes containing 10 ml of each of the following solutions:

| | |
|---|---|
| Tube 1 | medium 4 with 1 mM lanthanum nitrate; incubated aerobically |
| Tubes 2 & 3 | medium 4 with 1 mM lanthanum nitrate; incubated anaerobically |
| Tube 4 | medium 4 without metal; incubated anaerobically |

Samples were assayed as described previously.

Figure 3A:
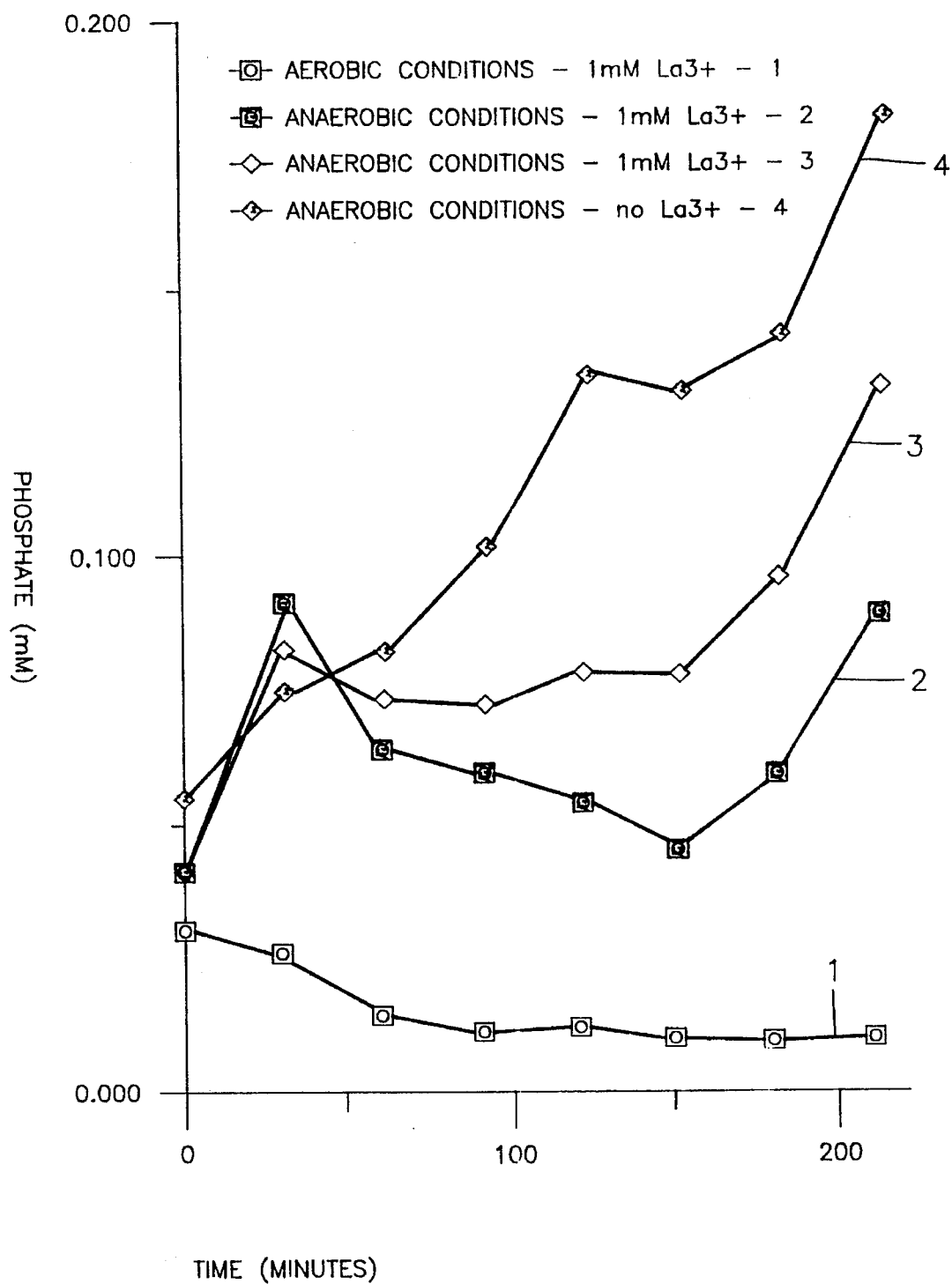

FIG. 3a shows that phosphate is released under anaerobic conditions and not under aerobic conditions: less phosphate is apparently released in tubes containing lanthanum. FIG. 3b also shows loss of lanthanum in tubes 2 and 3 concomitant with phosphate release. Significant lanthanum removal was not observed in Tube 1 under aerobic conditions indicating that there is little passive biosorption of the metal.

EXPERIMENT 5

Lanthanum removal by cell suspensions of strain W9

A culture of strain W9 was harvested after 24 h growth at a cell density ($OD_{600}$) of 1.000. The wet weight of the cell pellet obtained was 5.329 g and this was resuspended in a total volume of 6 ml. 1.5 ml of the suspension was added to tubes containing 20 ml of each of the following solutions:

| | |
|---|---|
| Tubes 1 & 2 | medium 4 with 0.7 mM lanthanum nitrate; incubated anaerobically |
| Tubes 3 & 4 | medium 4 without metal; incubated anaerobically |

Samples were assayed as described above.

Figure 4:
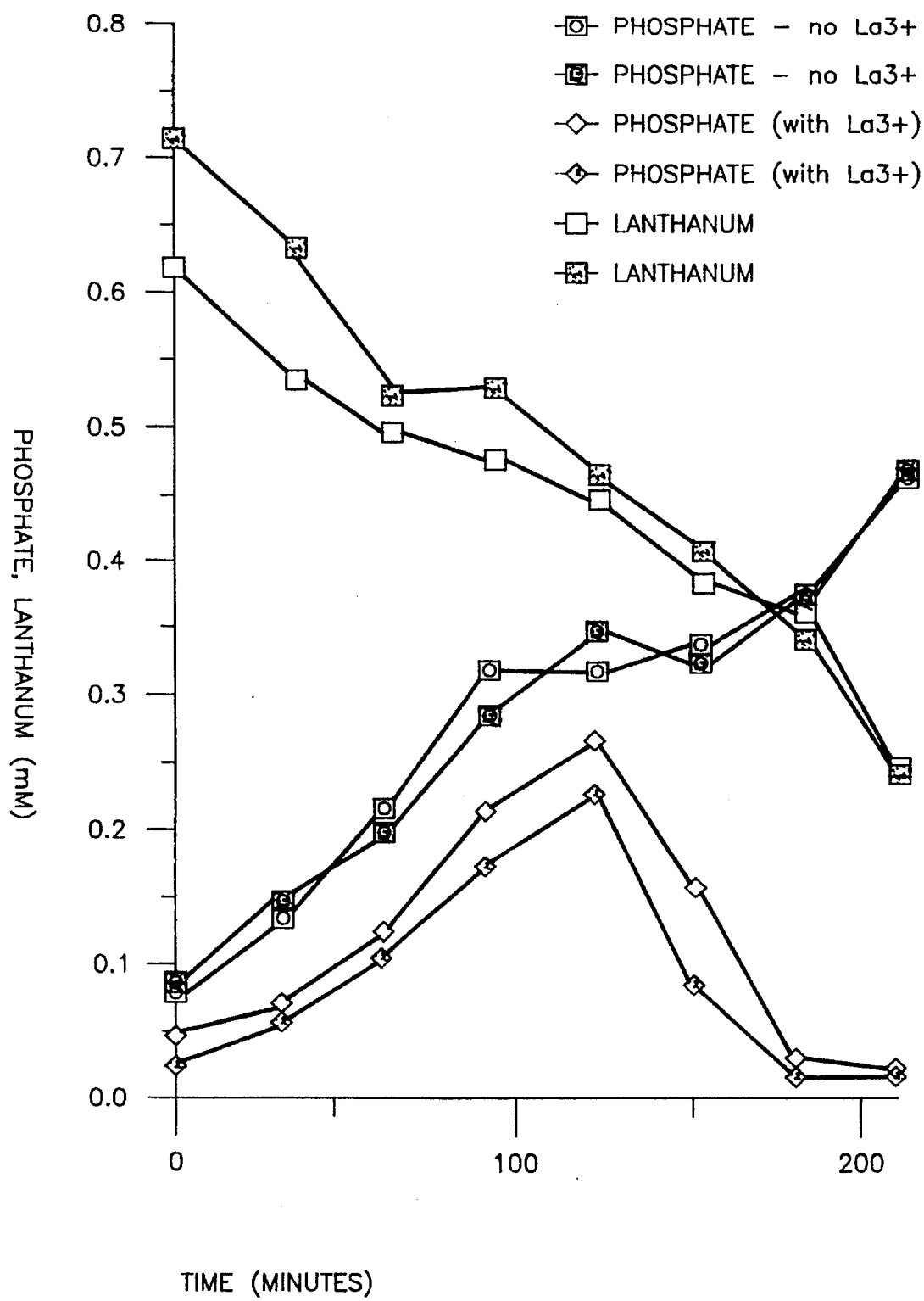

FIG. 4 shows phosphate release and lanthanum removal under anaerobic conditions with concomitant loss of lanthanum and an apparent reduction of phosphate release in the presence of lanthanum followed by a sudden loss of the released phosphate after 120 minutes. The reduction in the lanthanum concentration (0.4–0.5 mM) observed after 210 minutes is consistent with the release of 0.4–0.5 mM phosphate in the control tubes.

EXPERIMENT 6

Lanthanum removal by cell suspensions of isolate W6

A culture of strain W6 was harvested after 24 h growth at a cell density ($OD_{600}$) of 0.790. The wet weight of the cell pellet obtained was 3.80 g and this was resuspended in a total volume of 6 ml. 1.5 ml of the suspension was added to tubes containing 20 ml of each of the following solutions:

| | |
|---|---|
| Tubes 1 & 2 | medium 4 with 0.8 mM lanthanum nitrate; incubated anaerobically |
| Tubes 3 & 4 | medium 4 without metal; incubated anaerobically |

Samples were assayed as described above.

Figure 5:
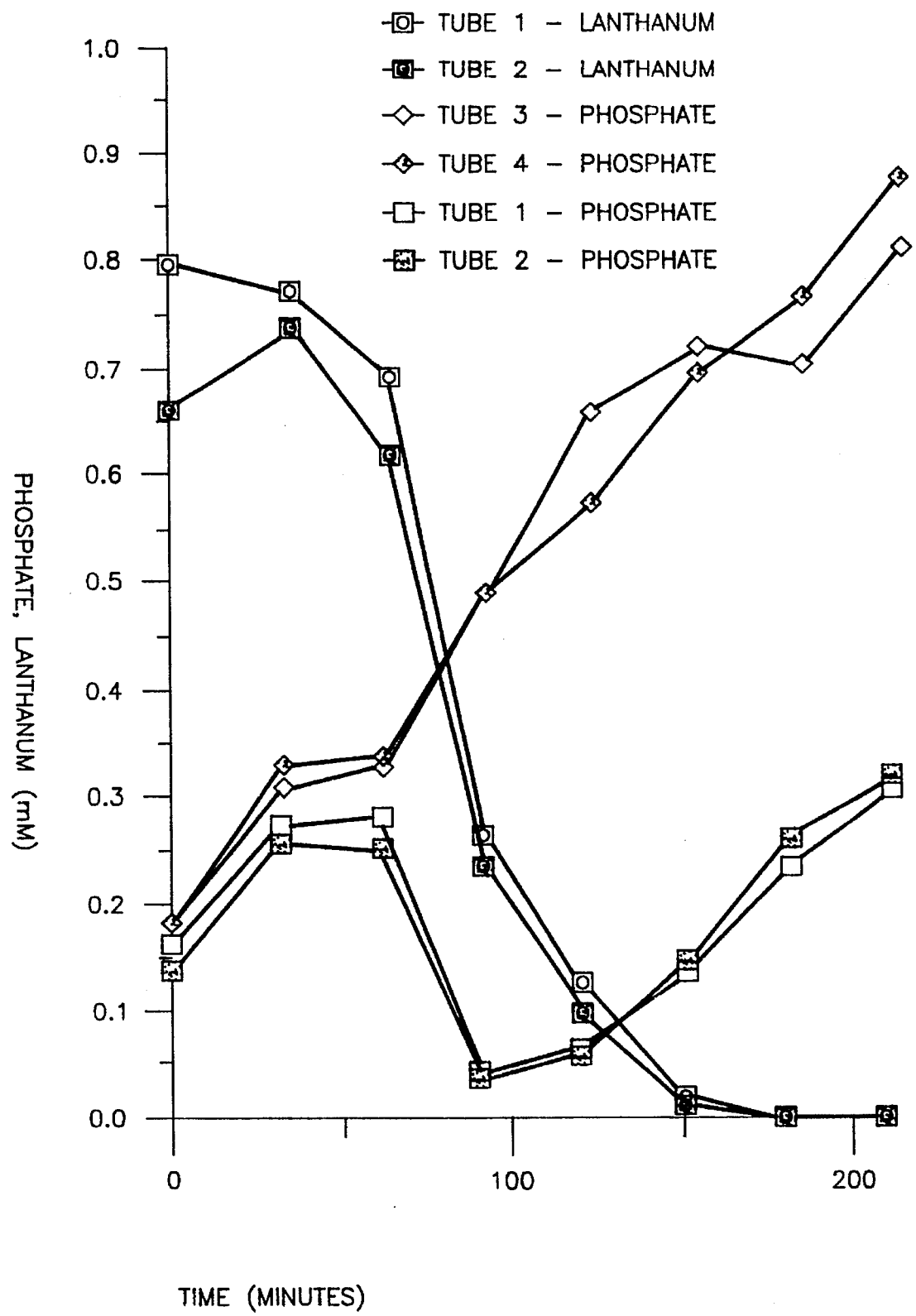

FIG. 5 shows phosphate release and lanthanum removal under anaerobic conditions with the loss of lanthanum and a sudden loss of the released phosphate started after 60 minutes. It will be noted that the complete removal of the 0.7–0.8 mM lanthanum occurred when 0.7–0.8 mM phosphate was detected in the control tubes (in the absence of metal).

EXPERIMENT 7

Removal of cadmium and lead in column reactors by immobilised cells of strain W9

A culture of strain W9 was grown and harvested as described previously and immobilised in agarose beads of mean diameter 1 mm. The beads were placed in pre-sterilised first and second columns with an approximate biomass loading of 5 g wet weight cells (100 g gelled material) per column, although due to diffusional limitations it is expected that not all the cells in a bead would contribute to the observed physiology of the immobilised culture; for example the diffusional limits for oxygen at a surface are usually taken to be 50 µm. The columns were subjected to anaerobic/aerobic cycling in the absence of metal for 8 days before metal was introduced: the first column received approximately 0.2 mM lead acetate, and the second column received approximately 0.2 mM cadmium acetate per anaerobic period over 7 consecutive days. Samples were analysed as described above.

Figure 6:
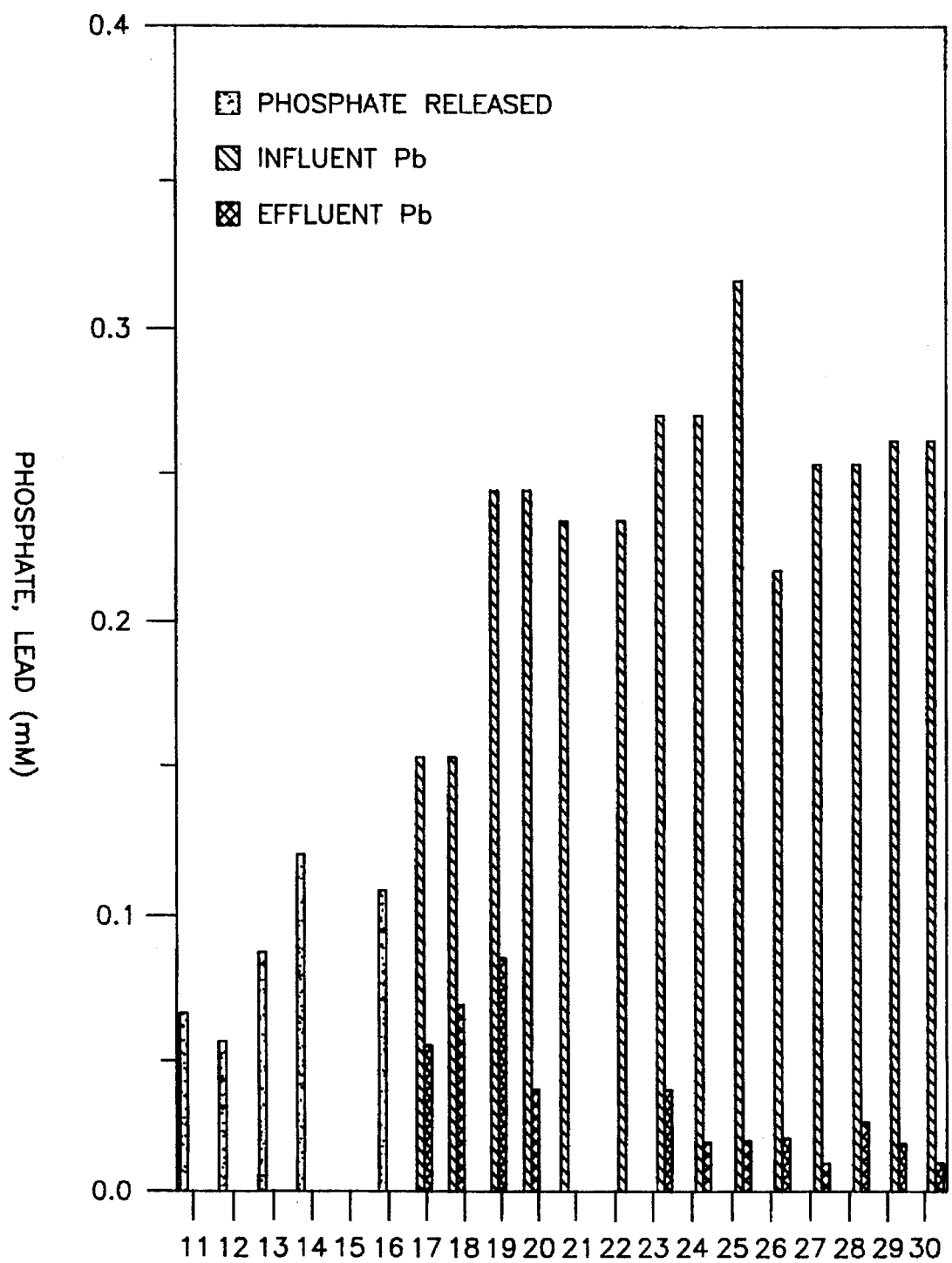
Figure 7:
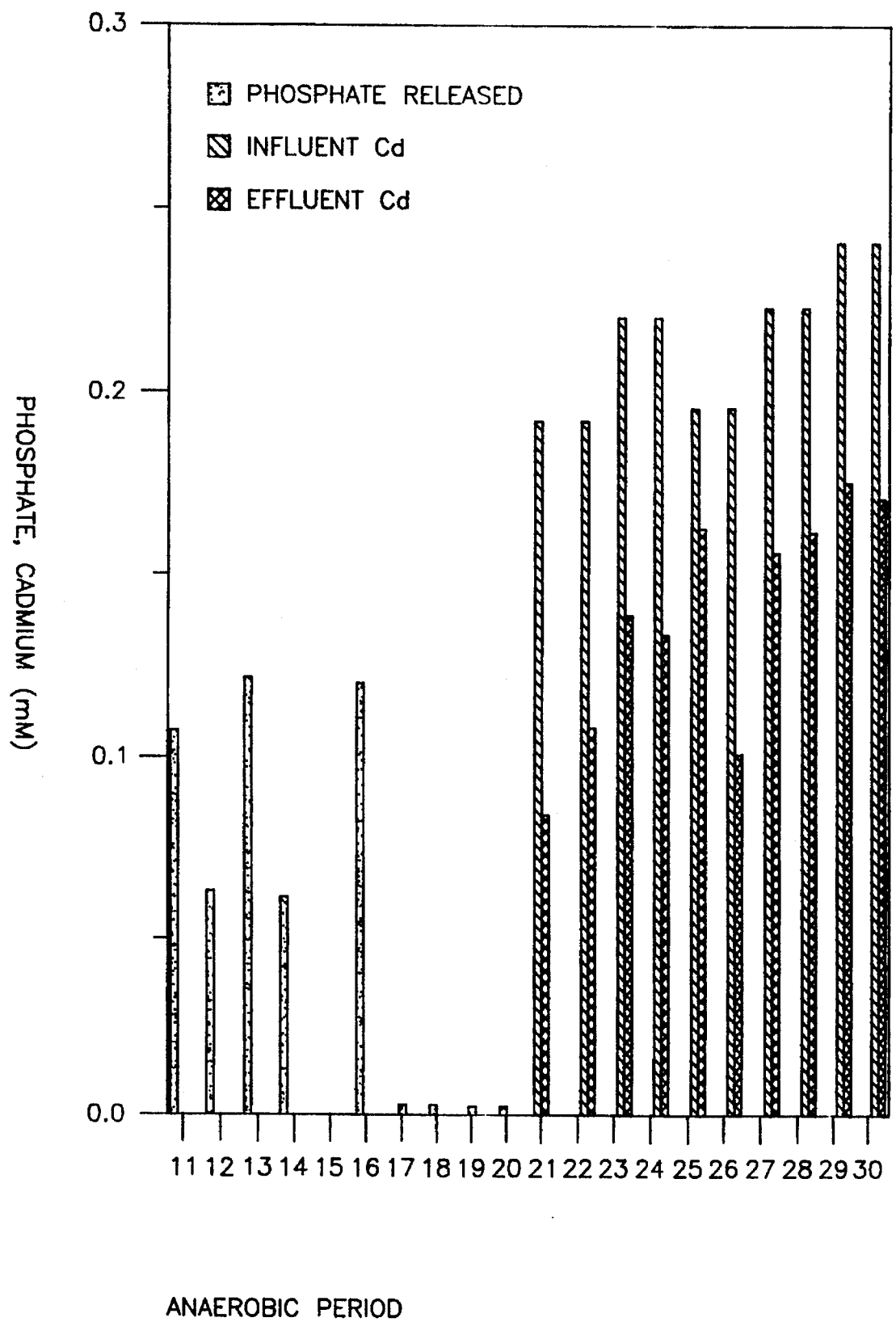

Table 3 below and FIG. 6 show the phosphate released and the lead determined in the influent and effluent of the first column. Table 4 below and FIG. 7 show the phosphate released and the cadmium determined in the influent and effluent of the second column.

TABLE 3

Phosphate release and lead removal in the first column

| | | | Polarography | | |
|---|---|---|---|---|---|
| Day | Time | mM $PO_4$ Released | Influent mg $Pb^{2+}$/l | Effluent mg $Pb^{2+}$/l | mM $Pb^{2+}$ Removed |
| 1 to 5 | | two anaerobic periods\day but no samples taken | | | |
| 6 | am | 0.066 | 0 | | |
| | pm | 0.056 | 0 | | |
| 7 | am | 0.086 | 0 | | |
| | pm | 0.119 | 0 | | |
| 8 | am | 0 | 0 | | |
| | pm | 0.106 | 0 | | |
| 9 | am | nt | 31.34 | 10.77 | 0.10 |
| | pm | nt | 31.34 | 13.63 | 0.09 |
| 10 | am | nt | 49.89 | 16.83 | 0.16 |

TABLE 3-continued

Phosphate release and lead removal in the first column

| Day | Time | mM PO$_4$ Released | Polarography Influent mg Pb$^{2+}$/l | Effluent mg Pb$^{2+}$/l | mM Pb$^{2+}$ Removed |
|---|---|---|---|---|---|
|  | pm | nt | 49.89 | 7.5 | 0.20 |
| 11 | am | nt | 47.58 | 0.063 | 0.23 |
|  | pm | nt | 47.58 | 0.06 | 0.23 |
| 12 | am | nt | 54.93 | 7.22 | 0.23 |
|  | pm | nt | 54.93 | 3.59 | 0.25 |
| 13 | am | nt | 64.19 | 3.62 | 0.29 |
|  | pm | nt | 43.79 | 3.66 | 0.19 |
| 14 | am | nt | 51.16 | 1.96 | 0.24 |
|  | pm | nt | 51.16 | 4.75 | 0.22 |
| 15 | am | nt | 52.61 | 3.02 | 0.24 |
|  | pm | nt | 52.61 | 1.58 | 0.25 |

(nt = not tested)

TABLE 4

Phosphate release and cadmium removal in the second column

| Day | Time | mM PO$_4$ Released | Polarography Influent mg Cd$^{2+}$/l | Effluent mg Cd$^{2+}$/l | mM Cd$^{2+}$ Removed |
|---|---|---|---|---|---|
| 1–5 |  | two anaerobic periods\day but no samples taken | | | |
| 6 | am | 0.105 | 0 | | |
|  | pm | 0.061 | 0 | | |
| 7 | am | 0.12 | 0 | | |
|  | pm | 0.059 | 0 | | |
| 8 | am | 0 | 0 | | |
|  | pm | 0.118 | 0 | | |
| 9 | am | nt | 0.25 | 0.015 | 0.00 |
|  | pm | nt | 0.25 | 0.013 | 0.00 |
| 10 | am | nt | 0.18 | 0.01 | 0.00 |
|  | pm | nt | 0.18 | 0.025 | 0.00 |
| 11 | am | nt | 21.26 | 9.21 | 0.11 |
|  | pm | nt | 21.26 | 11.83 | 0.08 |
| 12 | am | nt | 24.45 | 15.31 | 0.08 |
|  | pm | nt | 24.45 | 14.7 | 0.09 |
| 13 | am | nt | 21.64 | 17.99 | 0.03 |
|  | pm | nt | 21.64 | 11.06 | 0.09 |
| 14 | am | nt | 24.76 | 17.26 | 0.07 |
|  | pm | nt | 24.76 | 17.9 | 0.06 |
| 15 | am | nt | 26.75 | 19.39 | 0.07 |
|  | pm | nt | 26.75 | 18.93 | 0.07 |

(nt = not taken)

EXPERIMENT 8

Removal of lanthanum and uranium in automated reactors by immobilised cells of strain W6.

A culture of strain W6 was grown and harvested as described above, immobilised in agar, and the gel shredded to give particles approximately 1 mm ×1 mm×10 mm. The particles were placed in pre-sterilised first and second column reactors with an approximate biomass loading of 5 g wet weight cells (100 g gelled material) per column. The columns were subjected to anaerobic/aerobic cycling in the absence of metal for 7 days before metal was introduced: initially both reactors received 0.5 mM lanthanum nitrate, then the first reactor was continued on lanthanum while the second reactor received 0.2 mM uranyl nitrate. Samples were analysed as described above.

At the termination of the experiment when the reactors were drained, it was noted that a biofilm had developed on the glass beads at the base of the reactors. Samples of the gelled material and the biofilm on the beads in the second reactor were pale yellow in colour (uranyl phosphate is yellow) and were seen to fluoresce in UV light (as do pure crystals of uranyl phosphate). A portion of the gelled material and glass beads was shaken vigorously in acetone to remove surface bacteria and crystalline precipitate. The sample was dehydrated in acetone, evaporated, and analyzed by X-ray diffraction.

Figure 8:
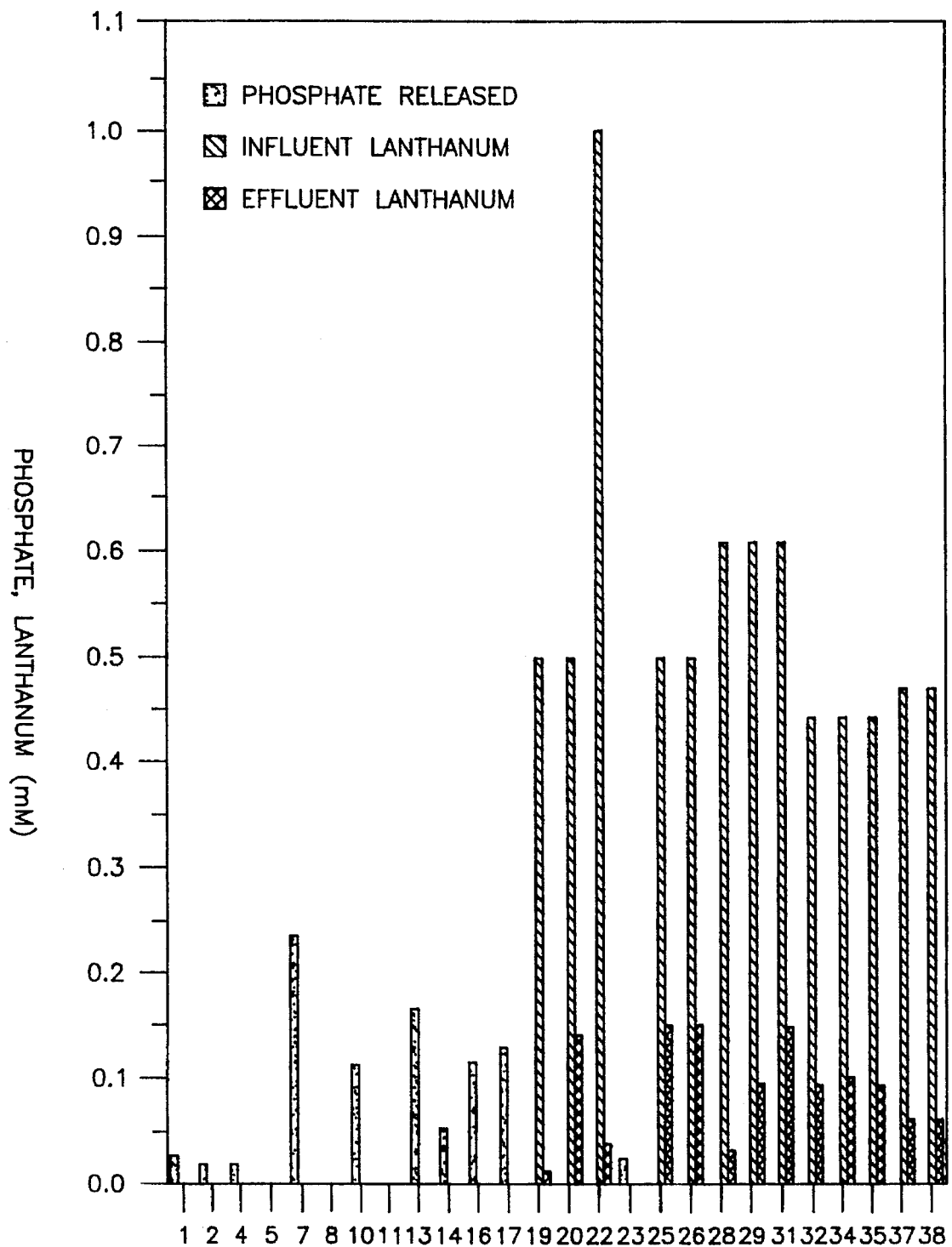
Figure 9:
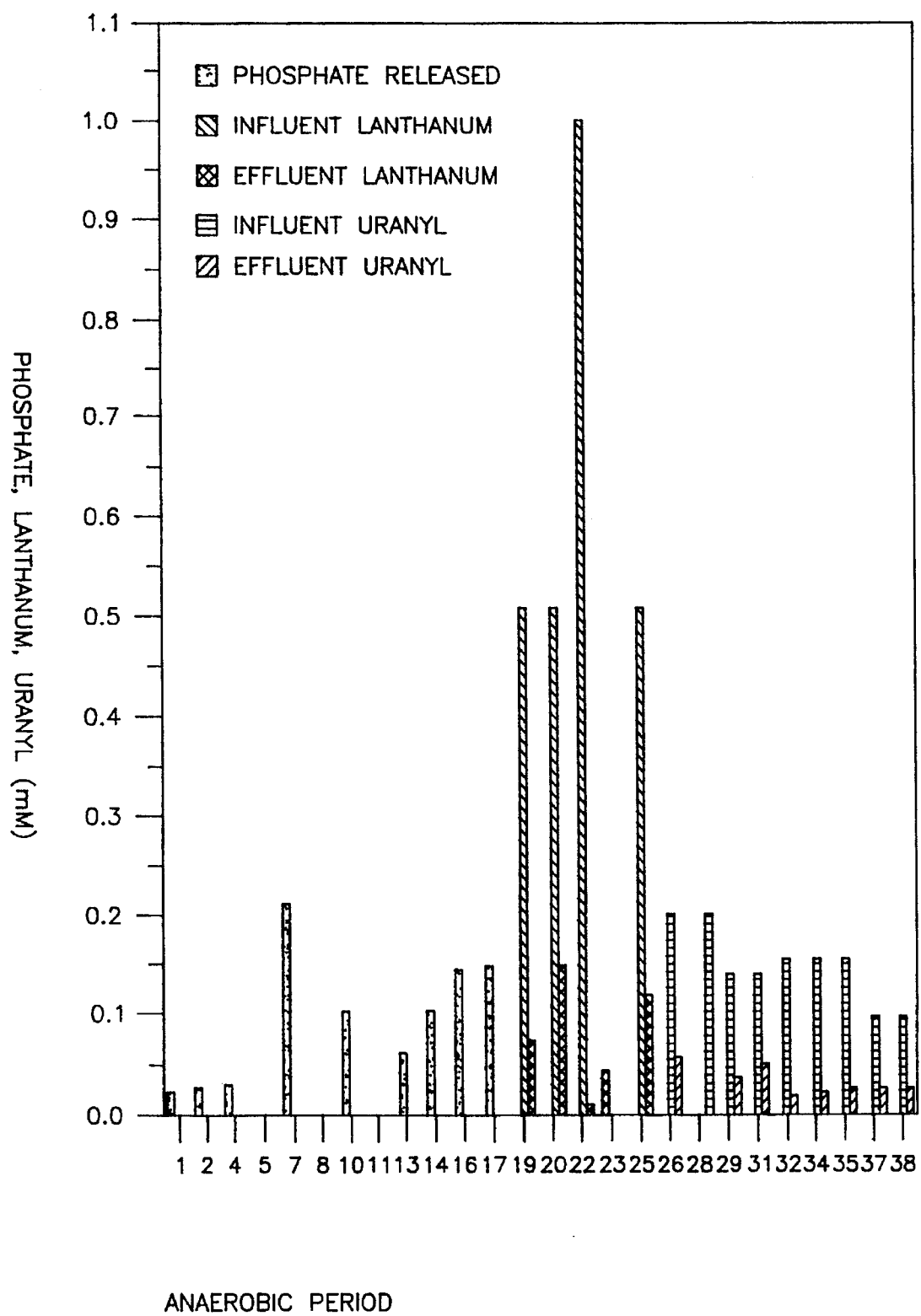
Figure 10:
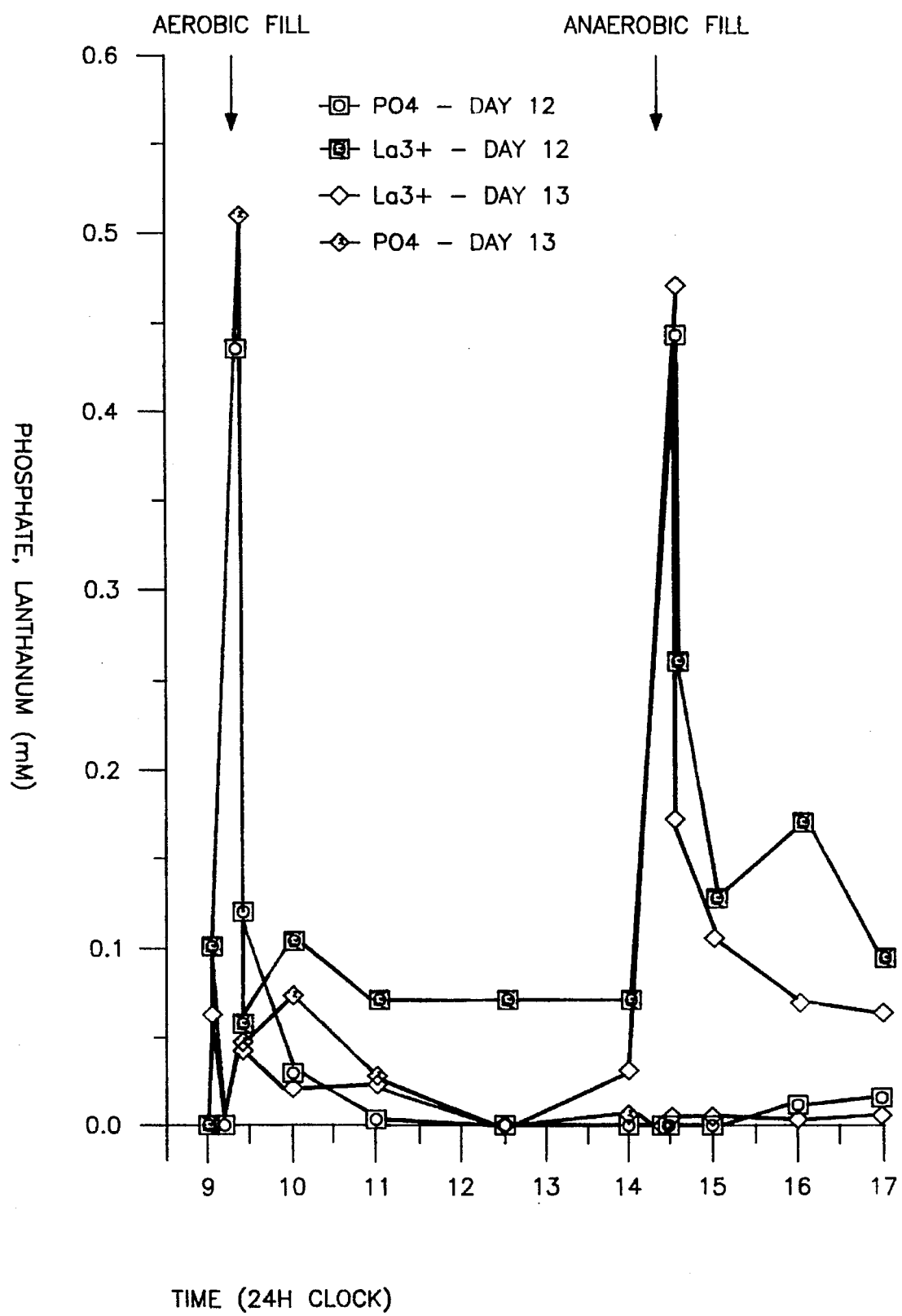
Figure 11:
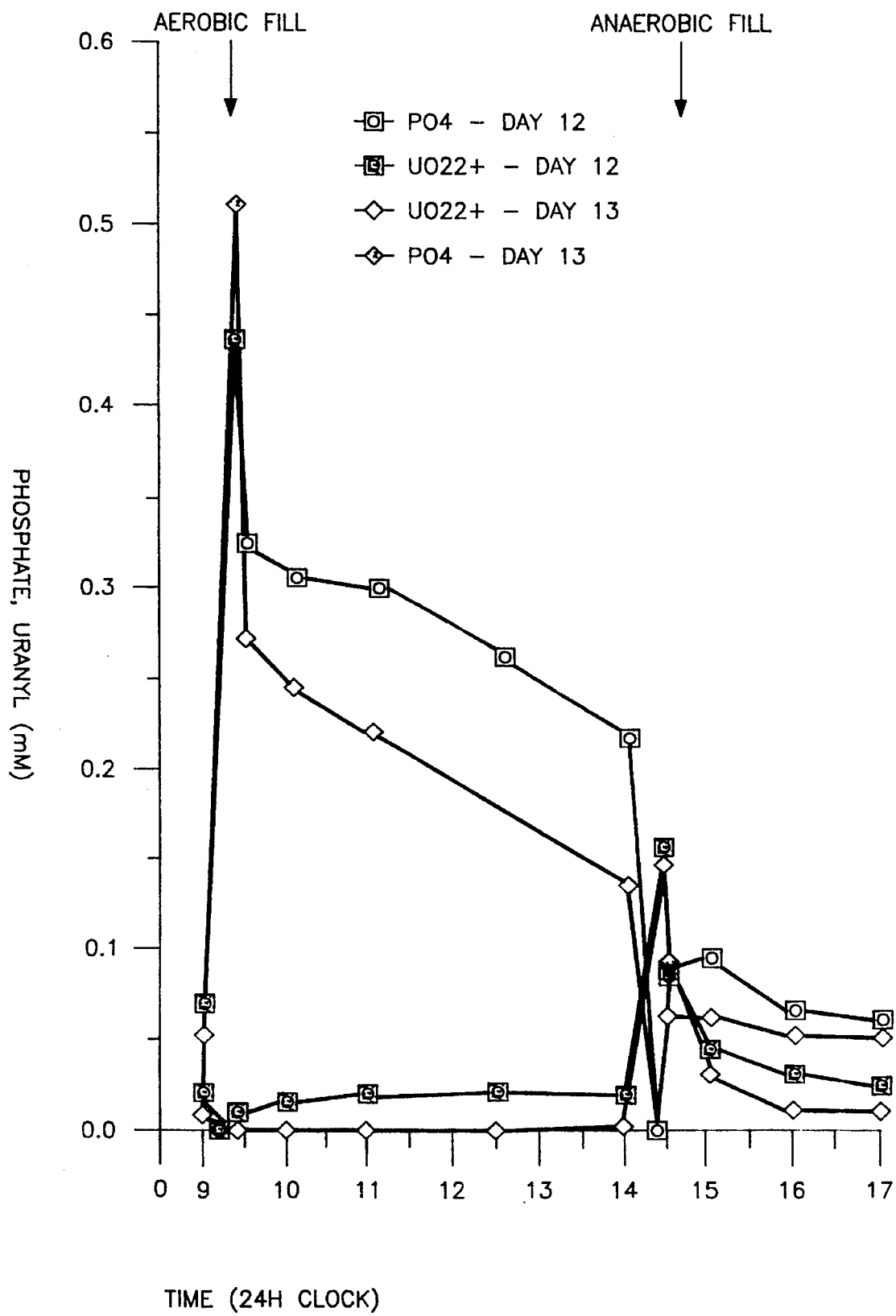

Table 5 below and FIG. 8 show the phosphate released and the lanthanum determined in the influent and effluent of the first reactor. Table 6 and FIG. 9 show the phosphate released and the lanthanum and uranyl determined in the influent and effluent of the second reactor. FIGS. 10 and 11 show that there was no appreciable solubilisation of the precipitated metals in the aerobic phase.

Figure 12:
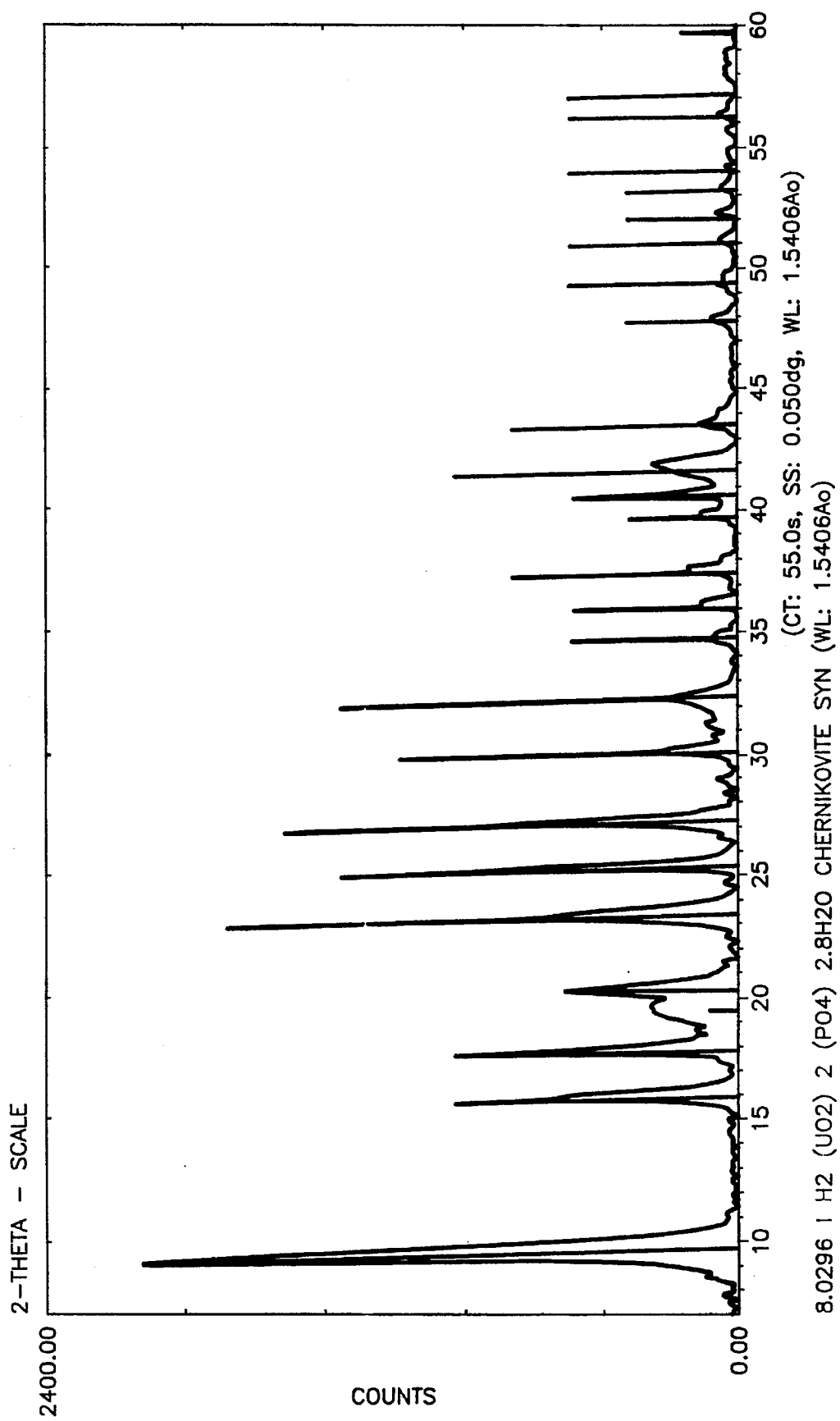

FIG. 12 shows that the spectrum obtained by X-ray diffraction pattern of the sample from the second reactor is consistent with that reported for $H_2(UO_2)_2(PO_4)_2 8H_2O$ (Ross (1955) Am. Mineral 40;917–919). The d values for the 10 strongest diffraction peaks are, respectively, within 0.03Å of those for $H_2(UO_2)_2(PO_4)_2.8H_2O$. This indicates that the sample contains crystalline material of $H_2(UO_2)_2(PO_4)_2.8H_2O$.

TABLE 5

Phosphate release and lanthanum removal by immobilized cells of strain W6 in reactor 1
3 anaerobic periods daily, samples only at 9:00 am and 5:00 pm

| Day | Time | mM PO$_4$ Released | Influent mM La$^{3+}$ | Effluent mM La$^{3+}$ | mM La$^{3+}$ Removed |
|---|---|---|---|---|---|
| 1 | am | 0.03 | 0 | | |
|  | pm | 0.02 | 0 | | |
| 2 | am | 0.02 | 0 | | |
|  | pm | nt | 0 | | |
| 3 | am | 0.24 | 0 | | |
|  | pm | nt | 0 | | |
| 4 | am | 0.11 | 0 | | |
|  | pm | nt | 0 | | |
| 5 | am | 0.16 | 0 | | |
|  | pm | 0.05 | 0 | | |
| 6 | am | 0.12 | 0 | | |
|  | pm | 0.13 | 0 | | |
| 7 | am | nt | 0.50 | 0.01 | 0.49 |
|  | pm | nt | 0.50 | 0.14 | 0.36 |
| 8 | am | nt | 1.00 | 0.04 | 0.96 |
|  | pm | 0.02 | 0.00 | 0.00 | 0.00 |
| 9 | am | nt | 0.50 | 0.15 | 0.35 |
|  | pm | nt | 0.50 | 0.15 | 0.35 |
| 10 | am | nt | 0.61 | 0.03 | 0.58 |
|  | pm | nt | 0.61 | 0.09 | 0.51 |
| 11 | am | nt | 0.61 | 0.15 | 0.46 |
|  | pm | nt | 0.44 | 0.09 | 0.35 |
| 12 | am | nt | 0.44 | 0.10 | 0.34 |
|  | pm | nt | 0.44 | 0.09 | 0.35 |
| 13 | am | nt | 0.47 | 0.06 | 0.41 |
|  | pm | nt | 0.47 | 0.06 | 0.41 | nt = not tested
Day 1 = anaerobic periods 1–3
Day 2 = anaerobic periods 4–6 etc

TABLE 6

Phosphate release and lanthanum and uranium removal by
immobilized cells of strain W6 in reactor 2
3 anaerobic periods daily, samples only at 9:00 am and 5:00 pm

| Day | Time | mM $PO_4$ Released | influent mM $La^{3+}$ | effluent mM $La^{3+}$ | mM $La^{3+}$ removed | influent mM $UO_2^{2+}$ | effluent mM $UO_2^{2+}$ | mM $UO_2^{2+}$ removed |
|---|---|---|---|---|---|---|---|---|
| 1 | am | 0.02 | 0 | | | 0 | | |
|   | pm | 0.03 | 0 | | | 0 | | |
| 2 | am | 0.03 | 0 | | | 0 | | |
|   | pm | nt | 0 | | | 0 | | |
| 3 | am | 0.21 | 0 | | | 0 | | |
|   | pm | nt | 0 | | | 0 | | |
| 4 | am | 0.10 | 0 | | | 0 | | |
|   | pm | nt | 0 | | | 0 | | |
| 5 | am | 0.06 | 0 | | | 0 | | |
|   | pm | 0.10 | 0 | | | 0 | | |
| 6 | am | 0.14 | 0 | | | 0 | | |
|   | pm | 0.15 | 0 | | | 0 | | |
| 7 | am | nt | 0.50 | 0.07 | 0.43 | 0 | | |
|   | pm | nt | 0.50 | 0.15 | 0.35 | 0 | | |
| 8 | am | nt | 1.00 | 0.01 | 0.99 | 0 | | |
|   | pm | 0.04 | 0 | | | 0 | | |
| 9 | am | nt | 0.50 | 0.12 | 0.38 | 0 | | |
|   | pm | nt | 0 | | | 0.20 | 0.05 | 0.15 |
| 10 | am | nt | 0 | | | 0.20 | nt | |
|    | pm | nt | 0 | | | 0.14 | 0.04 | 0.10 |
| 11 | am | nt | 0 | | | 0.14 | 0.05 | 0.09 |
|    | pm | nt | 0 | | | 0.16 | 0.02 | 0.14 |
| 12 | am | nt | 0 | | | 0.16 | 0.02 | 0.13 |
|    | pm | nt | 0 | | | 0.16 | 0.03 | 0.13 |
| 13 | am | nt | 0 | | | 0.10 | 0.03 | 0.07 |
|    | pm | nt | 0 | | | 0.10 | 0.03 | 0.07 | nt = not tested
Day 1 = anaerobic periods 1–3
Day 2 = anaerobic periods 4–6 etc

We claim:

1. A process for removing one or more metal ions from water, comprising the steps of cultivating a polyphosphate-accumulating microorganism in a culture medium under conditions where the microorganism can synthesise and utilise adenosine triphosphate (ATP); modifying ATP synthesis/utilisation whereby to cause the microorganism to utilize polyphosphate as an alternative energy source resulting in the production of phosphate ions; and reacting said phosphate ions with the metal ions so as to precipitate metal phosphate.

2. A process as claimed in claim 1, wherein said cultivating step is effected aerobically and the ATP synthesis/utilisation modifying step is effected by changing from aerobic to anaerobic conditions.

3. A process as claimed in claim 2, wherein said reacting step is effected by introducing the water containing said one or more metal ions after the aerobic cultivation step.

4. A process as claimed in any preceding claim 2, wherein the microorganism is a bacterium of the genus Acinetobacter.

5. A process as claimed in claim 1, wherein the microorganism has the polyphosphate-accumulating properties of Acinetobacter sp. W6 (NCIMB 40594) or Acinetobacter sp. W9 (NCIMB 40595).

6. A process as claimed in claim 1, wherein the cultivating step is effected in the presence of activated sludge containing said miroorganism.

7. A process claimed in claim 1, wherein said one or more metals are selected from cadmium, lead, copper, manganese, cobalt, nickel, calcium, strontium, yttrium, uranium, lanthanum, lanthanides, plutonium, americium and neptunium.

8. The use of one or more polyphosphate-accumulating microorganisms to accumulate polyphosphate which is then enzymatically cleaved in the presence of water containing one or more metals to produce phosphate ions which react with the metal(s) in the water in order to precipitate metal phosphate.

9. The use of phosphate ions produced upon cleavage of polyphosphate to remove metal(s) from solution by precipitation as metal phosphate(s).

10. The use of polyphosphate as the main source of phosphate for metal accumulation via enzymically mediated metal bioaccumulation or biomineralisation.

* * * * *